United States Patent
Liang et al.

(10) Patent No.: US 12,067,486 B2
(45) Date of Patent: Aug. 20, 2024

(54) SYSTEMS AND METHODS FOR FAULT DIAGNOSIS

(71) Applicant: SHANGHAI UNITED IMAGING INTELLIGENCE CO., LTD., Shanghai (CN)

(72) Inventors: Xinran Liang, Shanghai (CN); Xiang Sean Zhou, Shanghai (CN)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 1271 days.

(21) Appl. No.: 16/728,093

(22) Filed: Dec. 27, 2019

(65) Prior Publication Data
US 2020/0209109 A1 Jul. 2, 2020

(30) Foreign Application Priority Data
Dec. 28, 2018 (CN) .......................... 201811628678.9

(51) Int. Cl.
*G06N 3/08* (2023.01)
*G01M 13/00* (2019.01)
(Continued)

(52) U.S. Cl.
CPC .............. *G06N 3/08* (2013.01); *G01M 13/00* (2013.01); *G01R 33/28* (2013.01); *G06N 3/045* (2023.01); *G06N 3/047* (2023.01); *G16H 40/40* (2018.01)

(58) Field of Classification Search
CPC ...... G06N 3/08; G06N 3/0454; G06N 3/0472; G16H 40/40; G01R 33/28
See application file for complete search history.

(56) References Cited

U.S. PATENT DOCUMENTS 5,303,328 A * 4/1994 Masui .................. G06N 3/04
706/19
5,566,092 A 10/1996 Wang et al.
(Continued)

FOREIGN PATENT DOCUMENTS

CN 105136454 A 12/2015
CN 108956142 A 12/2018

OTHER PUBLICATIONS

Chuan, Fault Diagnosis for Rotating Machinery Using Vibration Measurement Deep Statistical Feature Learning, School of Mechanical Engineering, Dongguan University of Technology, China Department of Mechanical Engineering, Universidad Politécnica Salesiana, Cuenca 010105, Jun. 17, 2016) (Year: 2016).*

(Continued)

*Primary Examiner* — Lina Cordero
(74) *Attorney, Agent, or Firm* — METIS IP LLC

(57) ABSTRACT

A system for fault diagnosis is provided. The system may acquire a vibration signal of a target device, and determine one or more feature values of the vibration signal. The system may further determine a fault condition of the target device by applying a fault diagnosis model to the feature values. The fault diagnosis model may include a trained first component including a plurality of stacked trained RBMs, and a trained second component connected to the trained first component. The trained second component may include a trained fully connected layer and a trained output layer connected to the trained fully connected layer.

20 Claims, 12 Drawing Sheets

(51) Int. Cl.
*G01R 33/28* (2006.01)
*G06N 3/045* (2023.01)
*G06N 3/047* (2023.01)
*G16H 40/40* (2018.01)

(56) References Cited

U.S. PATENT DOCUMENTS

| | | | |
|---|---|---|---|
| 6,609,217 B1 * | 8/2003 | Bonissone | G16H 40/40 |
| | | | 714/26 |
| 2008/0314566 A1 * | 12/2008 | Chen | G01R 33/28 |
| | | | 165/104.33 |
| 2017/0091699 A1 | 3/2017 | Mueller | |
| 2019/0195727 A1 | 6/2019 | Jiang et al. | |
| 2021/0027182 A1 * | 1/2021 | Harris | G06N 20/00 |

OTHER PUBLICATIONS

Xiao-hui He, Dong Wang, Yan-feng Li, Chun-hua Zhou, "A Novel Bearing Fault Diagnosis Method Based on Gaussian Restricted Boltzmann Machine", Mathematical Problems in Engineering, vol. 2016, Article ID 2957083, 8 pages, 2016. https://doi.org/10.1155/2016/2957083 (Year: 2016).*

S. Xing, Y. Lei, F. Jia and J. Lin, "Intelligent fault diagnosis of rotating machinery using locally connected restricted boltzmann machine in big data era," 2017 IEEE International Conference on Industrial Engineering and Engineering Management (IEEM), Singapore, 2017, pp. 1930-1934 (Year: 2017).*

First Office Action in Chinese Application No. 201811628678.9 mailed on Jun. 3, 2020, 23 pages.

Gu, Lichen, Part 3: Trend analysis of dimensionless characteristic parameters, Trend Analysis and Deterioration Management of Equipment Operating Status, 2016, 7 pages.

* cited by examiner

900

SYSTEMS AND METHODS FOR FAULT DIAGNOSIS

CROSS-REFERENCE TO RELATED APPLICATIONS

This application claims priority to Chinese Patent Application No. 201811628678.9, filed on Dec. 28, 2018, the contents of which are hereby incorporated by reference.

TECHNICAL FIELD

The present disclosure generally relates to fault diagnosis, and more particularly, relates to systems and methods for fault diagnosis using a machine learning technique.

BACKGROUND

With the technology advancement, fault diagnosis and fault management play an increasing role in maintaining and monitoring mechanical devices. Compared with devices operating in a normal environment, the service life of devices that operate in a poor environment with e.g., a high magnetic field, a high radiation, a high temperature, may be more difficult to predict. In addition, for a device or a component of the device located in a concealed space, it may be difficult to diagnose a fault manually. A conventional approach for fault diagnosis may be performed by analyzing a vibration signal of a device. For example, the vibration signal may be converted from a time-domain signal to a frequency-domain signal by performing Fast Fourier Transformation, and a characteristic frequency corresponding to a certain failure type of the device may be extracted. However, the characteristic frequency corresponding to the failure type may be difficult to be extracted. For example, one or more additional signal processing operations, such as spectral envelope analysis and/or signal modulation, may need to be performed to extract the characteristic frequency. In addition, this conventional approach may be inefficient, and assumes or depends on a constant vibration speed of the device and/or an accurate measurement of the vibration speed. Therefore, it may be desirable to provide systems and methods for fault diagnosis with improved accuracy and efficiency.

SUMMARY

According to one aspect of the present disclosure, a system for fault diagnosis is provided. The system may include at least one storage device including a set of instructions, and at least one processor configured to communicate with the at least one storage device. When executing the set of instructions, the at least one processor may be configured to direct the system to acquire a vibration signal of a target device, and determine one or more feature values of the vibration signal. The at least one processor may further be configured to direct the system to determine a fault condition of the target device by applying a fault diagnosis model to the one or more feature values. The fault diagnosis model may include a trained first component including a plurality of stacked trained Restrictive Boltzmann Machines (RBMs), and a trained second component connected to the trained first component. The trained second component may include a trained fully connected layer and a trained output layer connected to the trained fully connected layer.

In some embodiments, the one or more feature values of the vibration signal may be determined in one or more of a frequency domain, a time domain, or a time-frequency domain.

In some embodiments, the one or more feature values of the vibration signal includes one or more of a Kurtosis factor, a Skewness factor, a Crest Factor, a clearance factor, a shape factor, an impulse indicator, a variance, a denominator of clearance factor, or an absolute mean value.

In some embodiments, the target device may be a medical imaging device or a portion thereof.

In some embodiments, the target device may include at least one of a cooling pump or a fan of a Magnetic Resonance Imaging (MRI) device.

In some embodiments, the trained RBMs of the trained first component may be energy-based models.

In some embodiments, the fault diagnosis model may be trained according to a model training process, and the trained first component and the trained second component may be trained in sequence during the model training process.

In some embodiments, the model training process may include obtaining a plurality of training samples and a preliminary model including a first component and a second component. Each of the plurality of training samples may include one or more sample feature values of a sample vibration signal of a sample device and a sample fault condition of the sample device. The first component may include a plurality of stacked RBMs, and the second component may include a fully connected layer and an output layer. The model training process may also include training the first component using the plurality of training samples. The model training process may further include generating the fault diagnosis model by training a compound model including the trained first component and the second component using the plurality of training samples. The fault diagnosis model may include the trained first component and the trained second component.

According to another aspect of the present disclosure, a system for generating a fault diagnosis model is provided. The system may include at least one storage device storing a set of instructions, and at least one processor configured to communicate with the at least one storage device. When executing the set of instructions, the at least one processor may be configured to direct the system to obtain a plurality of training samples and a preliminary model including a first component and a second component. Each of the plurality of training samples may include one or more sample feature values of a sample vibration signal of a sample device and a sample fault condition of the sample device. The first component may include a plurality of stacked RBMs, and the second component may include a fully connected layer and an output layer. The at least one processor may be configured to direct the system to train the first component using the plurality of training samples. The at least one processor may further be configured to direct the system to generate the fault diagnosis model by training a compound model including the trained first component and the second component using the plurality of training samples. The fault diagnosis model may include the trained first component and the trained second component.

In some embodiments, the first component may include a plurality of neurons. The training the first component may include an iterative operation including one or more iterations. At least one iteration of the iterative operation may include determining an energy level of each of the plurality of neurons in an updated first component determined in a previous iteration based on the at least one sample feature value of each training sample. The at least one iteration may also include determining whether a first termination condition is satisfied based on the determined energy levels. The at least one iteration may further include in response to a determination that the first termination condition is not satisfied, further updating the updated first component to be used in a next iteration.

In some embodiments, the determining whether a first termination condition is satisfied may include determining, among the energy levels of the plurality of neurons in the updated first component, a lowest energy level. The determining whether a first termination condition is satisfied may also include determining whether the lowest energy level exceeds a threshold energy level, and in response to a determination that the lowest energy level exceeds the threshold energy level, determining that the first termination condition is satisfied.

In some embodiments, the training a compound model including the trained first component and the second component may include an iterative operation including one or more iterations. At least one iteration of the iterative operation may include, for each of the plurality of training samples, determining a predicted fault condition of the corresponding sample device using an updated compound model determined in a previous iteration. The least one iteration may also include determining a value of a loss function based on the sample fault condition and the predicted fault condition of the sample device of each training sample. The least one iteration may further include determining whether a second termination condition is satisfied based on the value of the loss function. The at least one iteration may further include in response to a determination that the second termination condition is not satisfied, further updating the updated compound model to be used in a next iteration by updating, based on the value of the loss function, the second component in the updated compound model while maintaining the trained first component.

In some embodiments, for each of the plurality of training samples, the at least one sample feature value of the corresponding sample vibration signal may be determined in at least one of a frequency domain, a time domain, or a time-frequency domain.

In some embodiments, for each of the plurality of training samples, the at least one sample feature value of the corresponding sample vibration signal may include at least one of a Kurtosis factor, a Skewness factor, a Crest Factor, a clearance factor, a shape factor, an impulse indicator, a variance, a denominator of clearance factor, or an absolute mean value.

In some embodiments, the sample device of each of the plurality of training samples may include at least one of a cooling pump or a fan of a Magnetic Resonance Imaging (MRI) device.

According to another aspect of the present disclosure, a method for fault diagnosis implemented on a computing device having at least one processor and at least one storage device is provided. The method may include acquiring a vibration signal of a target device, and determining one or more feature values of the vibration signal. The method may further include determining a fault condition of the target device by applying a fault diagnosis model to the one or more feature values. The fault diagnosis model may include a trained first component including a plurality of stacked RBM, and a trained second component connected to the trained first component. The trained second component may include a trained fully connected layer and a trained output layer connected to the trained fully connected layer.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
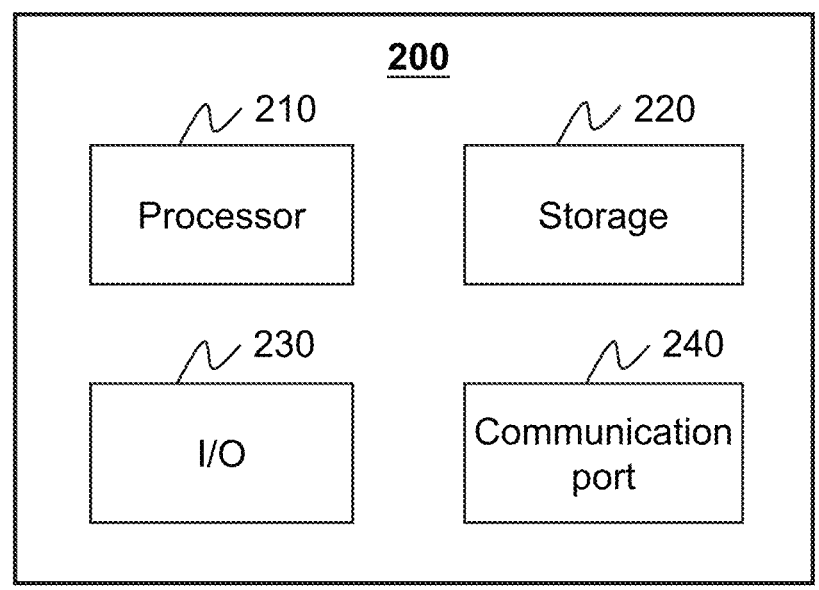
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items. The term "image" in the present disclosure is used to collectively refer to image data (e.g., scan data, projection data) and/or images of various forms, including a two-dimensional (2D) image, a three-dimensional (3D) image, a four-dimensional (4D), etc. The term "pixel" and "voxel" in the present disclosure are used interchangeably to refer to an element of an image.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

An aspect of the present disclosure relates to systems and methods for fault diagnosis. The systems and methods may acquire a vibration signal of a target device, and determine one or more feature values of the vibration signal. The systems and methods may further determine a fault condition of the target device by applying a fault diagnosis model to the feature value(s). By application of the fault diagnosis model, the systems and methods may perform fault diagnosis on the target device automatically. The fault diagnosis model may be trained to learn a complex mapping between input parameters (e.g., feature value(s) of a vibration signal) and the fault condition of a device from training data via a statistical approach using one or more machine-learning algorithms. The automated fault diagnosis as disclosed herein may obviate the need for extracting characteristic frequencies corresponding to different fault types, which may reduce manual debugging costs, save processing time, and improve the efficiency, accuracy, and/or consistency of fault diagnosis.

According to some embodiments of the present disclosure, the fault diagnosis model may include a trained first component and a trained second component connected to the trained first component. The trained first component may include a plurality of stacked trained RBMs. The trained second component may include a trained fully connected layer and a trained output layer connected to the trained fully connected layer. The fault diagnosis model may be regarded as a modification of a convolutional neural network (CNN) model, wherein convolutional layers of the CNN model may be replaced by the trained RBMs. The trained RBMs may be more suitable for processing one-dimensional features, such as the feature value(s) of the vibration signal. As such, the fault diagnosis model disclosed herein may result in a more accurate fault diagnosis result compared with the original CNN model.

In some embodiments, the fault diagnosis model may be generated by training a preliminary model according to a model training process. The preliminary model may include a first component and a second component, wherein the first component may include a plurality of stacked RBMs, and a second component may include a fully connected layer and an output layer. During the model training process, the first component and the second component may be trained separately according to different training strategies. For example, the first component may be trained iteratively according to an energy-based training strategy, during which energy levels of neurons of the first component may be determined and serve as a basis for updating the first component. After the first component is trained, a compound model including the trained first model and the second model may be trained to generate the fault diagnosis model. During the training of the compound model, a value of a loss function may be determined and the second component may be updated according to the loss function while the trained first component may be maintained without being updated. Because that the first component and the second component are suitable for different training strategies, training the first component and the second component separately using different training strategies may improve the accuracy and the reliability of the resulting fault diagnosis model.

Figure 1:
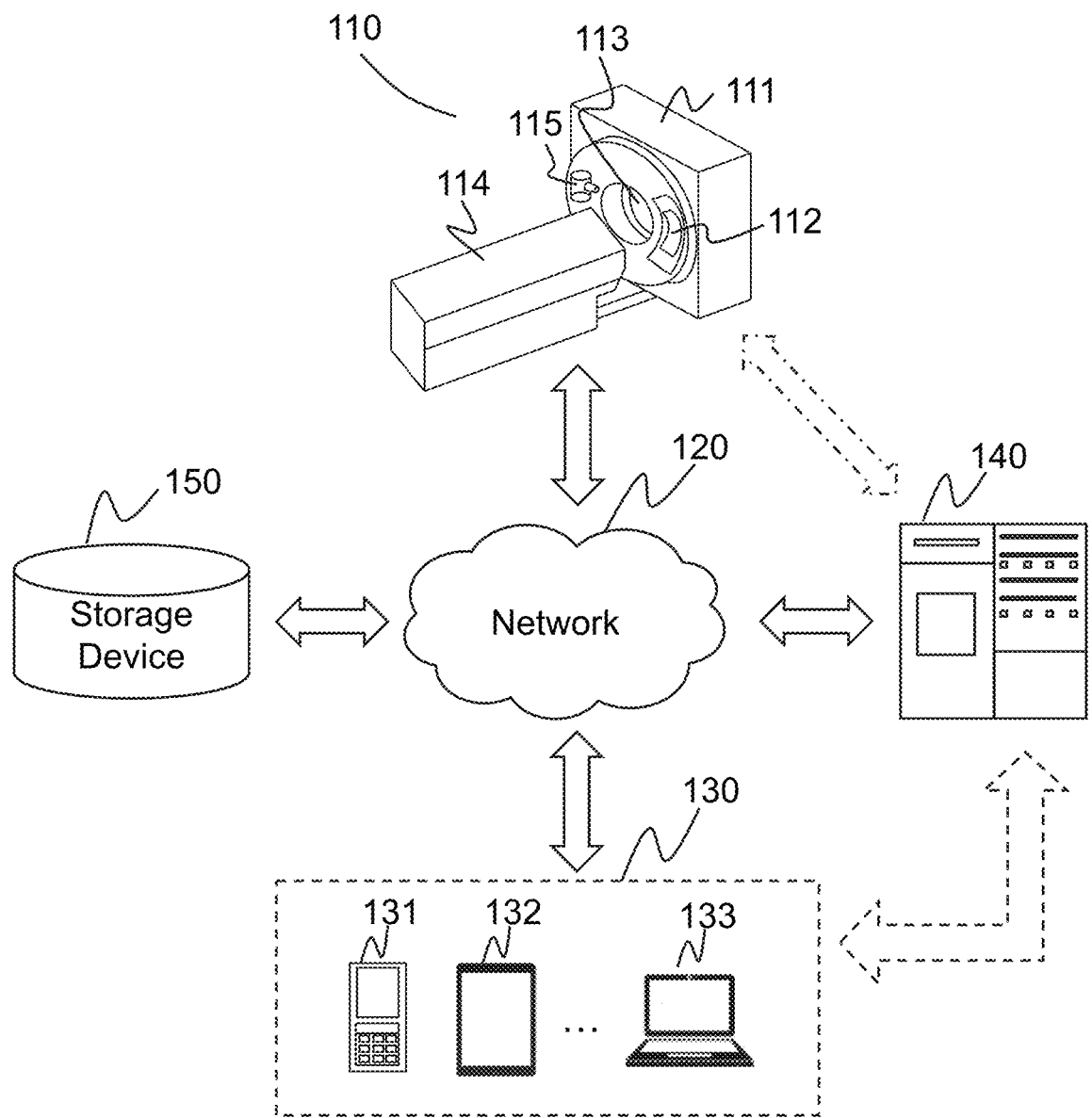
FIG. 1 is a schematic diagram illustrating an exemplary fault diagnosis system according to some embodiments of the present disclosure.

FIG. 1 is a schematic diagram illustrating an exemplary fault diagnosis system 100 according to some embodiments of the present disclosure. The fault diagnosis system 100 may be configured to perform fault diagnosis on a target device. The target device to be diagnosed may be of any type of devices. For illustration purposes, the following descriptions take an imaging device 110 as an exemplary target device, and not intended to limit the scope of the present disclosure.

As shown, the fault diagnosis system 100 may include the imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the fault diagnosis system 100 may be variable. Merely by way of example, the imaging device 110 may be connected to the processing device 140 through the network 120, as illustrated in FIG. 1. As another example, the imaging device 110 may be connected to the processing device 140 directly. As a further example, the storage device 150 may be connected to the processing device 140 through the network 120 or directly. As still a further example, a terminal 130 may be connected to the processing device 140 through the network 120 or directly.

The imaging device 110 may generate or provide image data related to an object via scanning the object. In some embodiments, the object may include a biological object and/or a non-biological object. For example, the object may include a specific portion of a body, such as a head, a thorax, an abdomen, or the like, or a combination thereof. In some embodiments, the imaging device 110 may include a single-modality imaging device and/or multi-modality imaging device. The single modality imaging device may include, for example, an X-ray imaging device, a computed tomography (CT) device, a magnetic resonance imaging (MRI) device, an ultrasonography device, a positron emission tomography (PET) device, an optical coherence tomography (OCT) imaging device, an ultrasound (US) imaging device, an intravascular ultrasound (IVUS) imaging device, a near infrared spectroscopy (NIRS) imaging device, a far infrared (FIR) imaging device, or the like, or any combination thereof. The multi-modality imaging device may include, for example, an X-ray imaging-magnetic resonance imaging (X-ray-MRI) device, a positron emission tomography-X-ray imaging (PET-X-ray) device, a single photon emission computed tomography-magnetic resonance imaging (SPECT-MRI) device, a positron emission tomography-computed tomography (PET-CT) device, a C-arm device, a digital subtraction angiography-magnetic resonance imaging (DSA-MRI) device, etc. In some embodiments, the image data relating to the object may include projection data, one or more images of the object, etc. The projection data may include raw data generated by the imaging device 110 by scanning the object and/or data generated by a forward projection on an image of the object.

In some embodiments, the imaging device 110 may include a gantry 111, a detector 112, a detecting region 113, a scanning table 114, and a radioactive scanning source 115. The gantry 111 may support the detector 112 and the radioactive scanning source 115. The object may be placed on the scanning table 114 to be scanned. The radioactive scanning source 115 may emit radioactive rays to the object. The radiation may include a particle ray, a photon ray, or the like, or a combination thereof. In some embodiments, the radiation may include a plurality of radiation particles (e.g., neutrons, protons, electron, μ-mesons, heavy ions), a plurality of radiation photons (e.g., X-ray, a γ-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

The network 120 may include any suitable network that can facilitate the exchange of information and/or data for the fault diagnosis system 100. In some embodiments, one or more components of the fault diagnosis system 100 (e.g., the imaging device 110, the processing device 140, the storage device 150, the terminal(s) 130) may communicate information and/or data with one or more other components of the fault diagnosis system 100 via the network 120. For example, the processing device 140 may obtain image data from the imaging device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the fault diagnosis system 100 may be connected to the network 120 to exchange data and/or information.

The terminal(s) 130 may be connected to and/or communicate with the imaging device 110, the processing device 140, and/or the storage device 150. For example, the terminal(s) 130 may receive a fault diagnosis result regarding the imaging device 110 (or a portion thereof) from the processing device 140, wherein the fault diagnosis result may be generated by the processing device 140 by application of a fault diagnosis model. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. In some embodiments, the terminal(s) 130 may be part of the processing device 140.

The processing device 140 may process data and/or information obtained from the imaging device 110, the storage device 150, the terminal(s) 130, or other components of the fault diagnosis system 100. In some embodiments, the processing device 140 may be a single server or a server group. The server group may be centralized or distributed. For example, the processing device 140 may process a plurality of sample vibration signals of one or more sample devices to generate a plurality of training samples for training a fault diagnosis model. The processing device 140 may further generate the fault diagnosis model by training a preliminary model using the training samples. As another example, the processing device 140 may apply the fault diagnosis model to perform fault diagnosis on a target device. In some embodiments, the training samples and/or the fault diagnosis model may be generated by a processing device, while the application of the fault diagnosis model may be performed on a different processing device. In some embodiments, the training samples and/or the fault diagnosis model may be generated by a processing device of a system different from the fault diagnosis system 100 or a server different from the processing device 140 on which the application of fault diagnosis model is performed. For instance, the training samples and/or the fault diagnosis model may be generated by a first system of a vendor who provides and/or maintains such a fault diagnosis model, while fault diagnosis on a target device based on the provided fault diagnosis model may be performed on a second system of a client of the vendor. In some embodiments, the application of the fault diagnosis model may be performed online in response to a request for fault diagnosis on a target device. In some embodiments, the training samples and/or the fault diagnosis model may be determined or generated offline.

In some embodiments, the fault diagnosis model may be determined and/or updated (or maintained) by, e.g., the manufacturer of the imaging device 110 or a vendor. For instance, the manufacturer or the vendor may load the fault diagnosis model into the fault diagnosis system 100 or a portion thereof (e.g., the processing device 140) before or during the installation of the imaging device 110 and/or the processing device 140, and maintain or update the fault diagnosis model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new fault diagnosis model) or a portion of a model tha-substitutes or supplements a corresponding portion of the model.

In some embodiments, the processing device 140 may be local to or remote from the fault diagnosis system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

In some embodiments, the processing device 140 may include one or more processors (e.g., single-core processor(s) or multi-core processor(s)). Merely by way of example, the processing device 140 may include a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

The storage device 150 may store data, instructions, and/or any other information. In some embodiments, the storage device 150 may store data obtained from the processing device 140, the terminal(s) 130, and/or the imaging device 110. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the fault diagnosis system 100 (e.g., the processing device 140, the terminal(s) 130). One or more components of the fault diagnosis system 100 may access the data or instructions stored in the storage device 150 via the network 120. In some embodiments, the storage device 150 may be part of the processing device 140.

It should be noted that the above description of the fault diagnosis system 100 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the fault diagnosis system 100 may include one or more additional components. Additionally or alternatively, one or more components of the fault diagnosis system 100 described above may be omitted. As another example, two or more components of the fault diagnosis system 100 may be integrated into a single component. In some embodiments, the fault diagnosis system 100 may be used to perform fault diagnosis on a device other than the imaging device 110.

FIG. 2 is a schematic diagram illustrating exemplary hardware and/or software components of a computing device 200 according to some embodiments of the present disclosure. The computing device 200 may be used to implement any component of the fault diagnosis system 100 as described herein. For example, the processing device 140 and/or the terminal 130 may be implemented on the computing device 200, respectively, via its hardware, software program, firmware, or a combination thereof. Although only one such computing device is shown, for convenience, the computer functions relating to the fault diagnosis system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the imaging device 110, the terminal(s) 130, the storage device 150, and/or any other component of the fault diagnosis system 100. In some embodiments, the processor 210 may include one or more hardware processors, such as a microcontroller, a microprocessor, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the imaging device 110, the terminal(s) 130, the storage device 150, and/or any other component of the fault diagnosis system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to generate a fault diagnosis model.

The I/O 230 may input and/or output signals, data, information, etc. In some embodiments, the I/O 230 may enable a user interaction with the processing device 140. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the processing device 140 and the imaging device 110, the terminal(s) 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
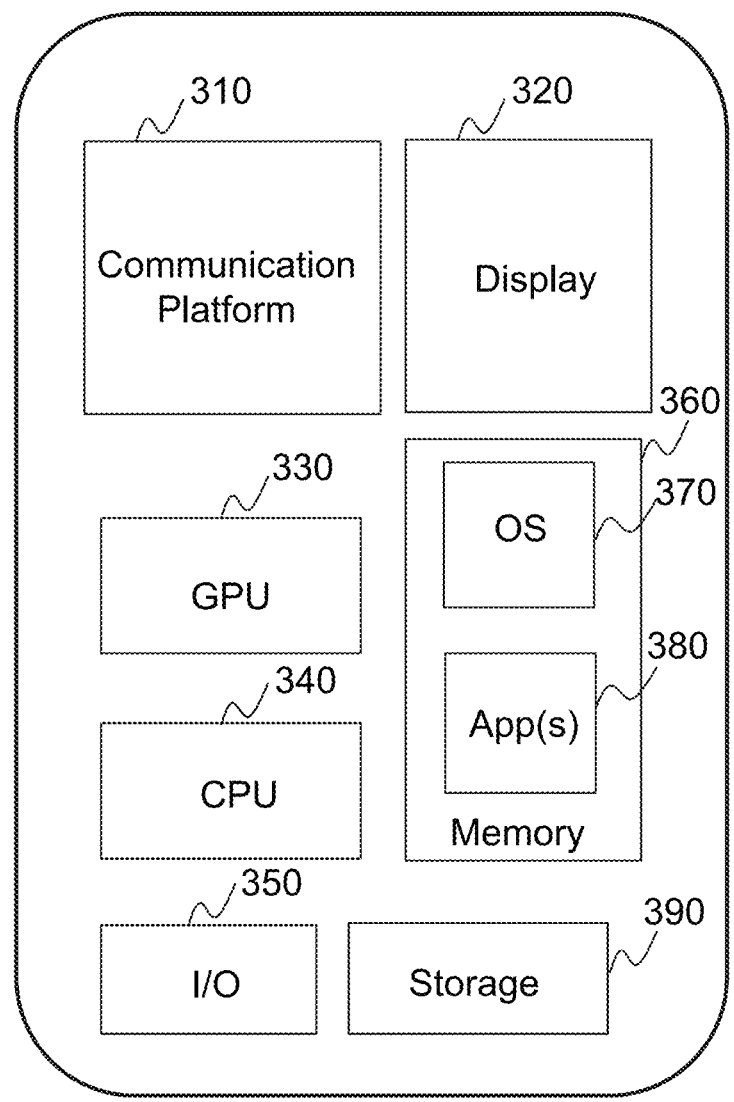
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components (e.g., a terminal 130 and/or the processing device 140) of the fault diagnosis system 100 may be implemented on the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to fault diagnosis or other information from the processing device 140. User interactions with the information stream may be achieved via the I/O 350 and provided to the processing device 140 and/or other components of the fault diagnosis system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
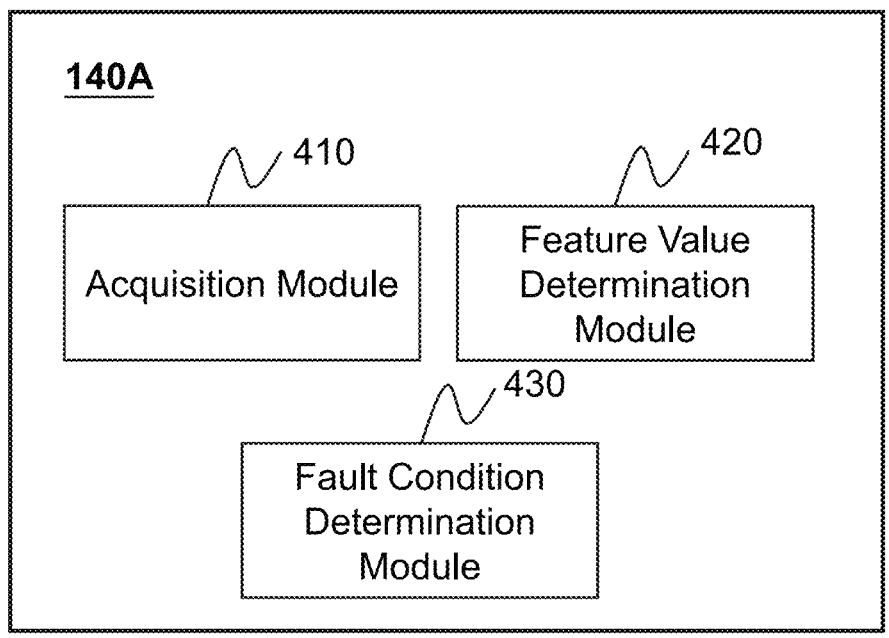
FIGS. 4A and 4B are block diagrams illustrating exemplary processing devices according to some embodiments of the present disclosure.
Figure 4B:
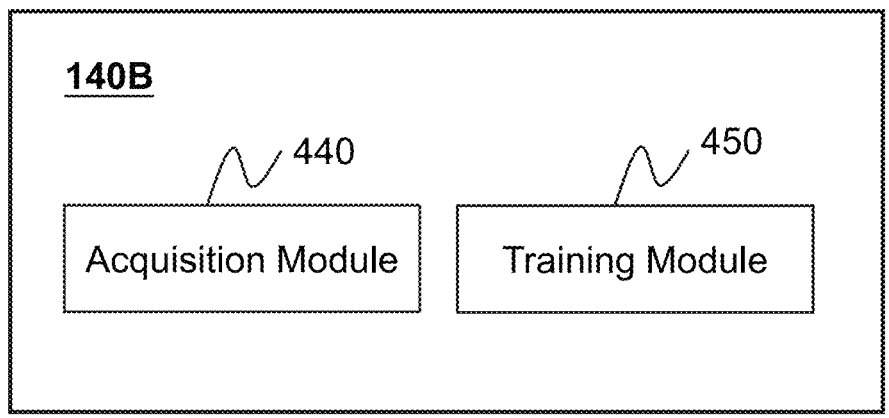

FIGS. 4A and 4B are block diagrams illustrating exemplary processing devices 140A and 140B according to some embodiments of the present disclosure. The processing devices 140A and 140B may be exemplary processing devices 140B as described in connection with FIG. 1. In some embodiments, the processing device 140A may be configured to perform fault diagnosis on a target device by application of a fault diagnosis model. The processing device 140B may be configured to generate the fault diagnosis model. In some embodiments, the processing devices 140A and 140B may be respectively implemented on a processing unit (e.g., a processor 210 illustrated in FIG. 2 or a CPU 340 as illustrated in FIG. 3). Merely by way of example, the processing devices 140A may be implemented on a CPU 340 of a terminal device, and the processing device 140B may be implemented on a computing device 200. Alternatively, the processing devices 140A and 140B may be implemented on a same computing device 200 or a same CPU 340. For example, the processing devices 140A and 140B may be implemented on a same computing device 200.

As shown in FIG. 4A, the processing device 140A may include an acquisition module 410, a feature value determination module 420, and a fault condition determination module 430.

The acquisition module 410 may be configured to acquire a vibration signal of the target device. The target device may be a device (e.g., a rotatory device) of any type, such as a bearing, a gear, a gear case, an electromotor, an engine, a draught fan, a supporting structure, a fan, a pump, a drill, a lathe, or the like, or any combination thereof. The vibration signal may include an original vibration signal in the time domain acquired by the vibration sensor, or a transformed vibration signal that is transformed from the original vibration signal. More descriptions regarding the acquisition of the vibration signal of the target device may be found elsewhere in the present disclosure. See, e.g., operation 502 and relevant descriptions thereof.

The feature value determination module 42 may be configured to determine one or more feature values of the vibration signal. As used herein, a feature value of the vibration signal refers to a value of a coefficient (e.g., a statistical coefficient) indicating a certain characteristic of the vibration signal. In some embodiments, the feature value(s) of the vibration signal may be determined in one or more of the frequency domain, the time domain, or the time-frequency domain. More descriptions regarding the determination of the feature values of the vibration signal may be found elsewhere in the present disclosure. See, e.g., operation 504 and relevant descriptions thereof.

The fault condition determination module 430 may be configured to determine a fault condition of the target device by applying a fault diagnosis model to the feature value(s). A fault diagnosis model refers to a neural network model configured to receive feature value(s) relating to a vibration signal of a certain device and output the fault condition of the device. The fault condition of the target device may indicate the operation status of the target device to be diagnosed, for example, whether the target device has a fault or not, a probability value that the target device has a fault, a fault type of the target device, a location at which a fault occurs, or the like, or any combination thereof. In some embodiments, the feature value(s) of the vibration signal may be inputted into the fault diagnosis model, and the fault diagnosis model may output the fault condition of the target device. Alternatively, the feature value(s) of the vibration signal may be inputted into the fault diagnosis model to obtain an output from the fault diagnosis model, and the fault condition determination module 430 may determine the fault condition of the target device based on the output of the fault diagnosis model. More descriptions regarding the determination of the fault condition of the target device may be found elsewhere in the present disclosure. See, e.g., operation 506 and relevant descriptions thereof.

As shown in FIG. 4B, the processing device 140B may include an acquisition module 440 and a training module 450.

The acquisition module 440 may be configured to obtain a plurality of training samples. Each training sample may include one or more sample feature values of a sample vibration signal of a sample device and a sample fault condition of the sample device. A sample device may be a device that has a known fault condition (also be referred to as the sample fault condition). A sample vibration signal of a sample device may refer to a vibration signal of the sample device. More descriptions regarding the training samples may be found elsewhere in the present disclosure. See, e.g., operation 802 and relevant descriptions thereof.

The acquisition module 440 may further be configured to obtain a preliminary model. The preliminary model may be any type of neural network model that is to be trained as the fault diagnosis model. In some embodiments, the preliminary model may include at least one RBM. In some embodiments, the preliminary model may include a first component including a plurality of stacked RBMs and a second component connected to the first component. The second component may include a fully connected layer and an output layer. More descriptions regarding the preliminary model may be found elsewhere in the present disclosure. See, e.g., operation 804 and relevant descriptions thereof.

The training module 450 may be configured to train the first component using the plurality of training sample. In some embodiments, the first component may be trained according to any suitable machine training algorithm, such as a greedy layer-wise unsupervised learning algorithm, a supervised learning algorithm, a Gibbs sampling contrastive divergence algorithm, or the like. The training of the first component may include an iterative operation including one or more iterations to iteratively update parameter value(s) of model parameter(s) of the first component. More descriptions regarding the training of the first component may be found elsewhere in the present disclosure. See, e.g., operation 806 and relevant descriptions thereof.

The training module 450 may further be configured to generate the fault diagnosis model by training a compound model including the trained first component and the second component using the plurality of training samples. After the first component is trained, the trained first component in combination with the second component may form the compound model. In some embodiments, the training of the compound model may include a second iterative operation including one or more second iterations to iteratively update parameter value(s) of model parameter(s) of the compound model. More descriptions regarding the generation of the fault diagnosis model may be found elsewhere in the present disclosure. See, e.g., operation 808 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and/or the processing device 140B may share two or more of the modules, and any one of the modules may be divided into two or more units. For instance, the processing devices 140A and 140B may share a same acquisition module; that is, the acquisition module 410 and the acquisition module 440 are a same module. In some embodiments, the processing device 140A and/or the processing device 140B may include one or more additional modules, such a storage module (not shown) for storing data. In some embodiments, the processing device 140A and the processing device 140B may be integrated into one processing device 140. In some embodiments, the determination of the set of training samples may be performed by a processing device, while the generation of the fault diagnosis model using the set of training samples may be performed by another processing device.

Figure 5:
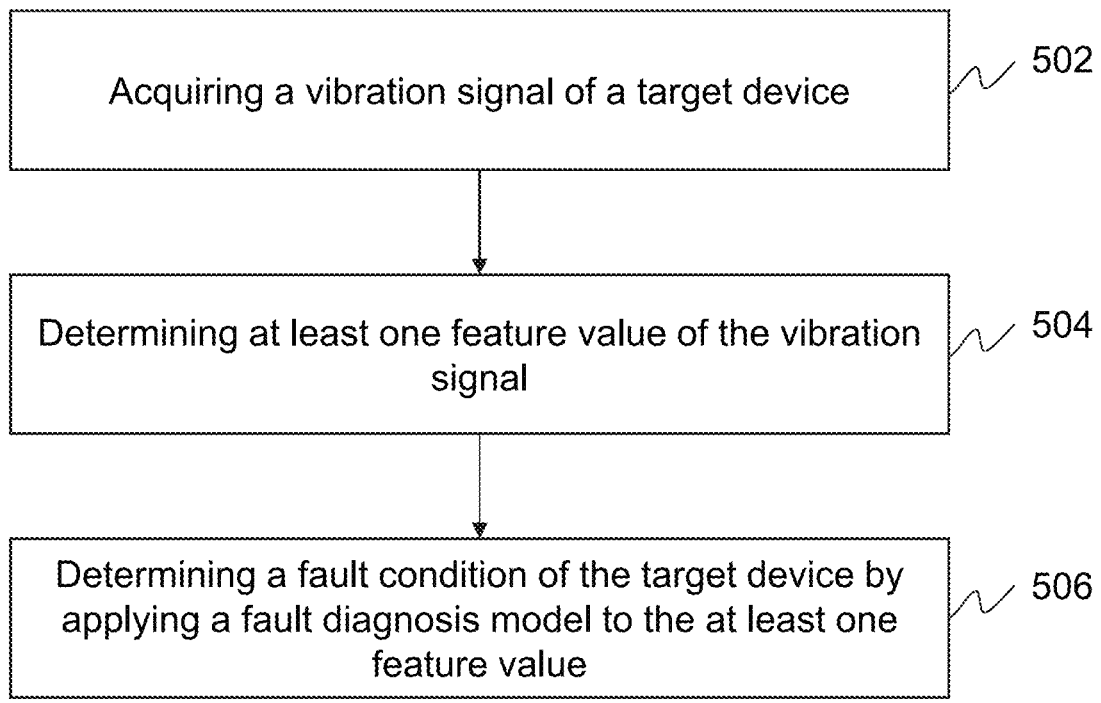
FIG. 5 is a flowchart illustrating an exemplary process for fault diagnosis according to some embodiments of the present disclosure.

FIG. 5 is a flowchart illustrating an exemplary process for fault diagnosis according to some embodiments of the present disclosure. In some embodiments, process 500 may be executed by the fault diagnosis system 100. For example, the process 500 may be implemented as a set of instructions (e.g., an application) stored in a storage device (e.g., the storage device 150, the storage 220, and/or the storage 390). In some embodiments, the processing device 140A (e.g., the processor 210 of the computing device 200, the CPU 340 of the mobile device 300, and/or one or more modules illustrated in FIG. 4A) may execute the set of instructions and may accordingly be directed to perform the process 500.

In 502, the processing device 140A (e.g., the acquisition module 410) may acquire a vibration signal of a target device.

The target device may be a device (e.g., a rotatory device) of any type, such as a bearing, a gear, a gear case, an electromotor, an engine, a draught fan, a supporting structure, a fan, a pump, a drill, a lathe, or the like, or any combination thereof. In some embodiments, the target device may be a medical imaging device or a portion thereof. Exemplary medical imaging devices may include an X-ray device, a CT device, an MRI device, an ultrasonography device, a PET device, an OCT device, an ultrasound device, an IVUS device, an MRS device, an FIR device, or the like, or any combination thereof. Exemplary portions of a CT device may include a bulb tube, a cooling system (e.g., a cooling pump), a fan, a supporting structure, a bearing, an electromotor, a detector, a table, or the like, or any combination thereof. Exemplary portions of an MRI device may include a coil, a cooling system (e.g., a cooling pump), a fan, a supporting structure, a bearing, an electromotor, a detector, a table, or the like, or any combination thereof. Exemplary portions of a PET device may include a cooling system (e.g., a cooling pump), a fan, a supporting structure, a bearing, an electromotor, a detector, a table, or the like, or any combination thereof.

In some embodiments, the vibration signal of the target device may be acquired from a vibration sensor mounted on or near the target device. For example, a three-axis vibration sensor may be mounted on the outer wall of a cooling pump to collect a vibration signal of the cooling pump. In some embodiments, the vibration signal of the target device may be acquired by the vibration sensor and transmitted to the processing device 140A in real time or intermittently (e.g., periodically or irregularly), for example, 10 times per minute.

Figure 9:
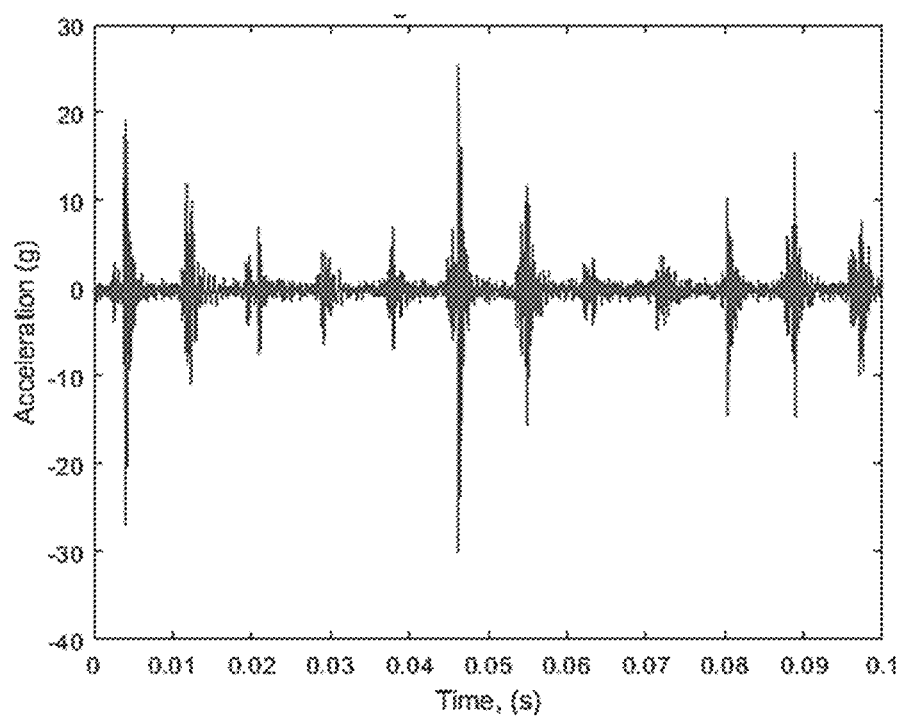
FIG. 9 is a schematic diagram illustrating an exemplary vibration signal in the time domain according to some embodiments of the present disclosure.
Figure 10:
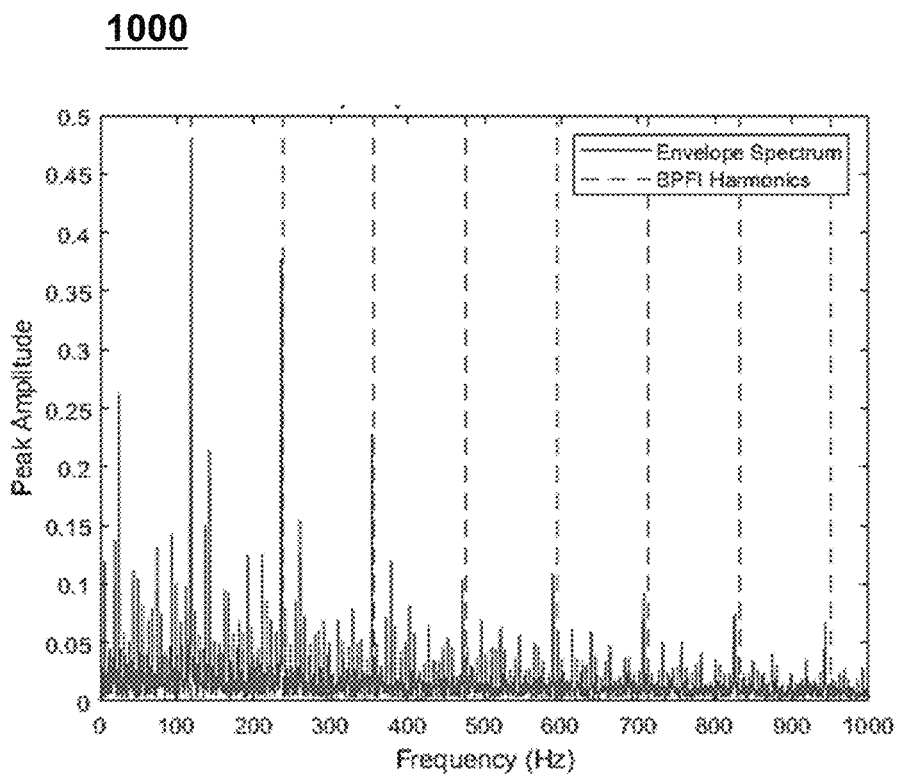
FIG. 10 is a schematic diagram illustrating an exemplary transformed vibration signal in the frequency domain according to some embodiments of the present disclosure.
Figure 11A:
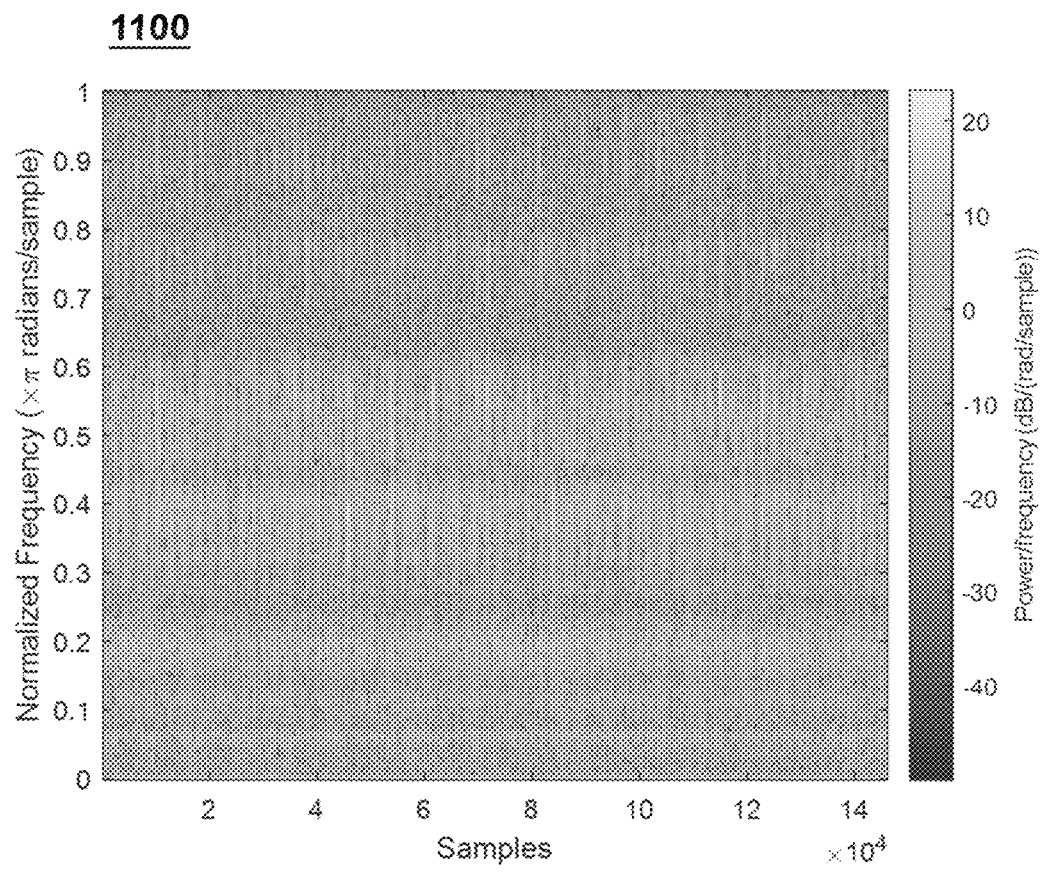
FIG. 11A is a schematic diagram illustrating an exemplary transformed vibration signal in the time-frequency domain according to some embodiments of the present disclosure.

In some embodiments, the vibration signal may include an original vibration signal in the time domain acquired by the vibration sensor. For example, the vibration signal may include an exemplary vibration signal 900 in the time domain as illustrated in FIG. 9. The vibration signal 900 was acquired by a three-axis vibration sensor mounted on the outer wall of a cooling pump. Additionally or alternatively, the vibration signal may include a transformed vibration signal that is transformed from the original vibration signal, such as a first transformed vibration signal in the frequency domain and/or a second transformed vibration signal in the time-frequency domain. For example, the vibration signal may include a transformed vibration signal 1000 in the frequency domain as illustrated in FIG. 10. The transformed vibration signal 1000 was transformed from the vibration signal 900 by performing fast Fourier transformation. The full line in FIG. 10 represents an envelope spectrum of the transformed vibration signal 1000, and the dotted line in FIG. 10 represents a ball passing frequency inner race (BPFI) and the Harmonic of the BPFI extracted from the transformed vibration signal 1000. As another example, the vibration signal may include a transformed vibration signal 1100 in the time-frequency domain as illustrated in FIG. 11A.

In some embodiments, a transformed vibration signal may be transformed from the original vibration signal by the processing device 140A or another computing device (e.g., a processor of the vibration sensor) by performing signal transformation including, such as a Fourier transformation (e.g., a fast Fourier transformation), a wavelet transformation, a Laplace Transform, a sine transformation, a cosine transformation, z-transformation. The wavelet transformation may include a continuous wavelet transformation (CWT), a discrete wavelet transformation (DWT), a wavelet packet transformation (WPT), or the like, or any combination thereof.

Merely by way of example, a transformed vibration signal X(f) in the frequency domain may be transformed from a vibration signal x(t) in the time domain by performing Fourier transformation according to Equation (1) as below:

$$X(f)=\hat{x}(f)=\int_{-\infty}^{+\infty}x(t)e^{-2\pi j'ft}dt, \quad \text{Equation (1)}$$

where j' refers to an imaginary number, f refers to the frequency, and t refers to the time.

As another example, a transformed vibration signal in the time-frequency domain may be transformed from the original vibration signal by performing a wavelet transformation, such as a CWT, a DWT, a WPT, or the like, or any combination thereof. In some embodiments, the WPT, which may have relatively fewer decomposition dimensions and be suitable for processing high-frequency signals (e.g., a signal having a frequency higher than a threshold frequency), may be performed to generate the transformed vibration signal in the time-frequency domain. For example, by performing WPT, the original vibration signal x(t) may be decomposed into a plurality of wavelet packet nodes by one or more low-pass filters and/or one or more high-pass filters according to Equation (2) as below:

$$p_{j,k}{}^n = \int_{-\infty}^{+\infty} x(t) W_{j,k}{}^n(t) d(t),  \quad \text{Equation (2)}$$

where $p_{j,k}{}^n$ refers to a wavelet packet node, W(t) refers to a reference wavelet function or a mother wavelet function, j refers to an integral scaling factor associated with an expansion ratio of the wavelet packet node, k refers to a translation factor that specifies a translated distance of the wavelet packet node along a certain direction, and n refers to an oscillation factor.

In some embodiments, the vibration signal obtained in 502 may include a vibration signal in the time domain, a vibration signal in the frequency domain, and a vibration signal in the time-frequency domain, which may be represented according to Equation (3) to (5), respectively, as below:

$$M(p, q) = \begin{cases} x(t); p \in R^1, q = t \in R^{n_0}, & \text{Equation (3)} \\ X(f); p \in R^1, q = f \in R^{[\frac{n_0}{2}]}, & \text{Equation (4)} \\ [P_{1,k}^1, P_{1,k}^2, \ldots, P_{j,k}^{2^j}]; p \in R^{2^{j+1}-1}, q \in R^{\frac{n_0}{2^j}}. & \text{Equation (5)} \end{cases}$$

where p refers to the index number to distinguish different equations, $n_0$ refers to the length of the signal, $R^1$ refers to a one-dimensional real number, and q refers to the time sequence, or the frequency sequence, or the time-frequency sequence index. For example, p=1 to a, or the first set refers to time domain equations; p=(a+1) to b refers frequency domain equations, and =(b+1) to c refers to wavelet equations. The exact value of a, b, and c may depend on how many equations is employed in a model (e.g., a fault diagnosis model as described elsewhere in this disclosure).

In 504, the processing device 140A (e.g., the feature value determination module 420) may determine one or more feature values of the vibration signal.

Figure 11B:
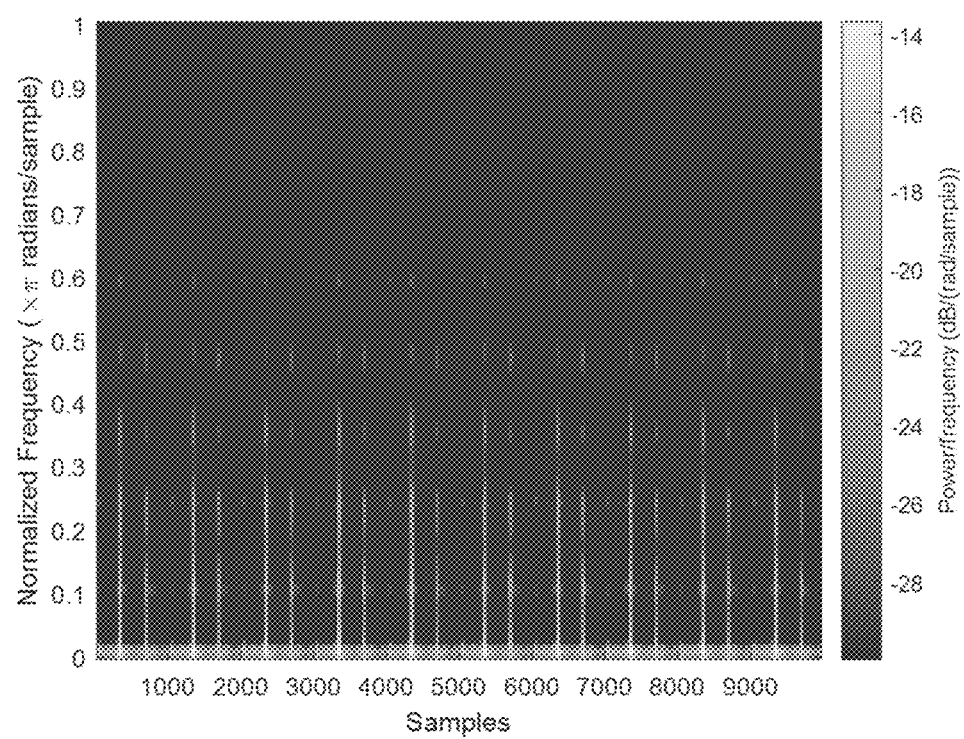
FIG. 11B is a schematic diagram illustrating exemplary feature values extracted from the transformed vibration signal FIG. 11A according to some embodiments of the present disclosure.

As used herein, a feature value of the vibration signal may refer to a value of a coefficient (e.g., a statistical coefficient) indicating a certain characteristic of the vibration signal. Merely by way of example, the feature value(s) of the vibration signal may include a Kurtosis factor $F_1$, a Skewness factor $F_2$, a Crest Factor $F_3$, a clearance factor $F_4$, a shape factor $F_5$, an impulse indicator $F_6$, a variance $F_7$, a denominator of clearance factor $F_8$, an absolute mean value $F_9$, or the like, or any combination thereof. In some embodiments, the feature value(s) of the vibration signal may be determined in at least one of the frequency domain, the time domain, or the time-frequency domain. For example, the vibration signal obtained in 502 may be the original vibration signal in the time domain acquired by a vibration sensor. The processing device 140A may transform the original vibration signal into a first transformed vibration signal in the frequency domain and/or a second transformed vibration signal in the time-frequency domain, and determine feature value(s) in the frequency domain and/or the time-frequency domain. As another example, the vibration signal obtained in 502 may include the original vibration signal, the first transformed vibration signal, and the second transformed vibration signal. The processing device 140A may determine feature value(s) for each of the original vibration signal, the first transformed vibration signal, and the second transformed vibration signal. Merely by way of example, the processing device 140A may determine feature values of the transformed vibration signal 1100 in FIG. 11A, and the feature values may be represented in FIG. 11B.

In some embodiment, the feature values $F_1$ to $F_9$ may be determined in each of the frequency domain, the time domain, and the time-frequency domain, thereby generating 27 feature values. In some embodiments, the feature values $F_1$ to $F_9$ may be determined according to Equations (6) to (14), respectively, as below:

$$F_1 = \frac{\int (X - \mu)^4 Pr(X) dX}{\sigma^4}, \quad \text{Equation (6)}$$

$$F_2 = \frac{\int (X - \mu)^3 Pr(X) dX}{\sigma^3}, \quad \text{Equation (7)}$$

$$F_3 = \frac{\max(X)}{\sqrt{\frac{1}{N}\sum_{i=1}^{N}\sqrt{X_i^2}}}, \quad \text{Equation (8)}$$

$$F_4 = \frac{\max(X)}{\sqrt{\frac{1}{N}\sum_{i=1}^{N}\sqrt{X_i}}}, \quad \text{Equation (9)}$$

$$F_5 = \frac{\sqrt{\frac{1}{N}\sum_{i=1}^{N}\sqrt{X_i^2}}}{\frac{1}{N}\sum_{i=1}^{N}|X_i|}, \quad \text{Equation (10)}$$

$$F_6 = \frac{\max(X)}{\frac{1}{N}\sum_{i=1}^{N}|X_i|}, \quad \text{Equation (11)}$$

$$F_7 = \int (X - \mu)^2 Pr(X), \quad \text{Equation (12)}$$

$$F_8 = \left(\frac{1}{N}\sum_{i=1}^{N}\sqrt{X_i}\right)^2, \quad \text{Equation (13)}$$

and $$F_9 = \frac{1}{N}\sum_{i=1}^{N}|X_i|, \quad \text{Equation (14)}$$

where N refers to the length of X(t) or X(f), Pr(X) refers to a probability density, X refers to a signal data sequence or a transformed signal data sequence, $X_i$ refers to an $i^{th}$ element of the signal data sequence or the transformed signal data sequence, μ refers to a mean value, and σ refers to a variance.

In some embodiments, the processing device 140A may preprocess the vibration signal obtained in 502, and determine one or more feature values of the preprocessed vibration signal. The preprocessing of the vibration signal may include a signal filtering, a signal enhancement, a noise reduction, or the like, or any combination thereof.

In 506, the processing device 140A (e.g., the fault condition determination module 430) may determine a fault condition of the target device by applying a fault diagnosis model to the feature value(s).

As used herein, a fault diagnosis model may refer to a neural network model configured to receive feature value(s) relating to a vibration signal of a certain device and output the fault condition of the device. The fault condition of target device may indicate the operation status of the target device to be diagnosed, for example, whether the target device has a fault or not, a probability value that the target device has a fault, a fault type of the target device, a location at which a fault occurs, or the like, or any combination thereof. For example, the target device may be a bearing including an inner race, an outer race, a plurality of balls, and a bearing frame. The fault condition of the bearing may include a fault type of the bearing, such as an outer race fault, an inner race fault, a ball fault, a bearing frame fault, or the like, or any combination thereof.

In some embodiments, the feature value(s) of the vibration signal obtained in 504 may be inputted into the fault diagnosis model, and the fault diagnosis model may output the fault condition of the target device. Alternatively, the feature value(s) of the vibration signal obtained in 504 may be inputted into the fault diagnosis model to obtain an output from the fault diagnosis model, and the processing device 140A may determine the fault condition of the target device based on the output of the fault diagnosis model. Merely by way of example, the fault diagnosis model may output a probability value that the target device has a fault, and the processing device 140A may determine whether the target device has a fault based on the probability value. In some embodiments, if the probability value that the target device has a fault exceeds an upper limit, such as 70%, the target device may be considered having a high probability of fault. If the probability value is less than a lower limit, such as 30%, the target device may be considered having a low probability of fault. If the probability value is in a range from lower limit to upper limit, the target device may be considered as having a medium probability of fault, and the processing device 140A may transmit a notification to a user of the fault diagnosis system 100 (e.g., a maintenance personnel) to further check the target device. In some embodiments, if the fault condition of the target device indicates that the target device has a fault or has a high probability (or medium probability) of fault, the processing device 140A may transmit a notification to a terminal device of user of the fault diagnosis system 100 (e.g., a maintenance personnel). The notification may be in the form of, for example, a message, a sound, a vibration, a light, or the like, or any combination thereof.

In some embodiments, the fault diagnosis model may be obtained from one or more components of the fault diagnosis system 100 or an external source via a network (e.g., the network 120). For example, the fault diagnosis model may be previously trained by a computing device (e.g., the processing device 140B), and stored in a storage device (e.g., the storage device 150, the storage 220, and/or the storage 390) of the fault diagnosis system 100. The processing device 140A may access the storage device and retrieve the fault diagnosis model. In some embodiments, the fault diagnosis model may be generated according to a machine learning algorithm. The machine learning algorithm may include but not be limited to an artificial neural network algorithm, a deep learning algorithm, a decision tree algorithm, an association rule algorithm, an inductive logic programming algorithm, a support vector machine algorithm, a clustering algorithm, a Bayesian network algorithm, a reinforcement learning algorithm, a representation learning algorithm, a similarity and metric learning algorithm, a sparse dictionary learning algorithm, a genetic algorithm, a rule-based machine learning algorithm, or the like, or any combination thereof. The machine learning algorithm used to generate the fault diagnosis model may be a supervised learning algorithm, a semi-supervised learning algorithm, an unsupervised learning algorithm, or the like. In some embodiments, the fault diagnosis model may be generated by a computing device (e.g., the processing device 140B) by performing a process (e.g., process 800) for generating a fault diagnosis model disclosed herein. More descriptions regarding the generation of the fault diagnosis model may be found elsewhere in the present disclosure. See, e.g., FIG. 8 and relevant descriptions thereof.

Figure 6:
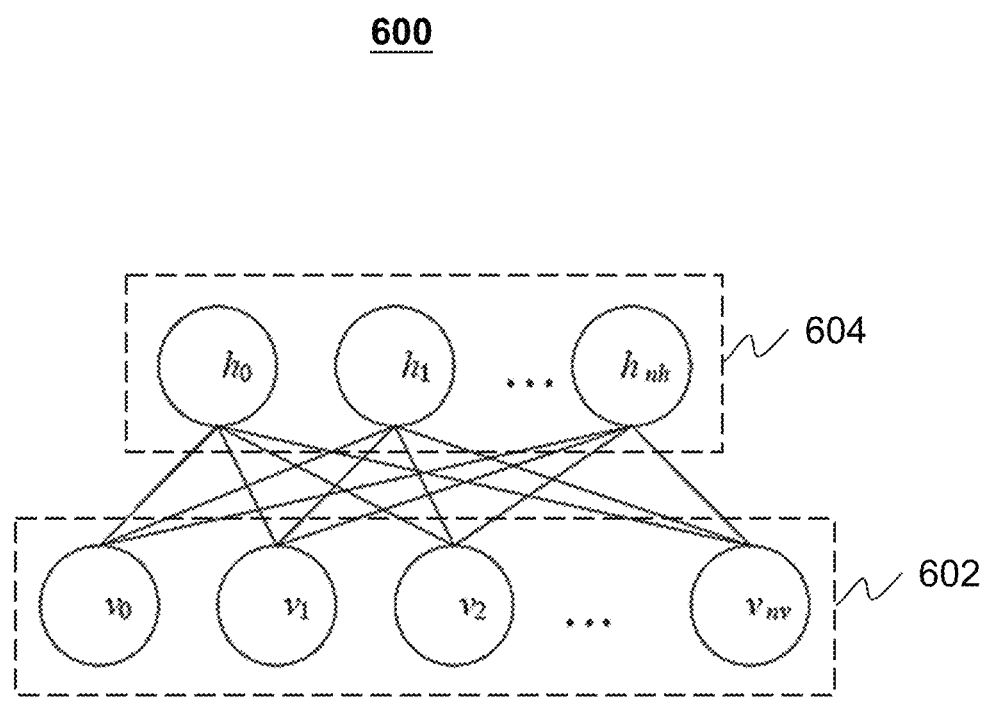
FIG. 6 is a schematic diagram illustrating an exemplary Restrictive Boltzmann Machine (RBM) according to some embodiments of the present disclosure.

In some embodiments, the fault diagnosis model may include at least one trained RBM. For illustration purposes, FIG. 6 illustrates an exemplary trained RBM 600 according to some embodiments of the present disclosure. As shown in FIG. 6, the trained RBM 600 may include a visible layer 602 (or represented by v) and a hidden layer 604 (or represented by h). The visible layer 602 may include a plurality of visible neurons. The hidden layer 604 may include a plurality of hidden neurons. For example, the count of the visible neurons of the visible layer 602 may be equal to nv, and the $i^{th}$ visible neuron in the visible layer 602 may have a state $v_i$. The count of the hidden neurons of the hidden layer 604 may be equal to nh, and the $j^{th}$ hidden neuron in the hidden layer 604 may have a state $h_j$ as shown in FIG. 6. The visible layer 602 may be configured to receive an input of the trained RBM 600. For example, one feature value of the vibration signal of the target device may be inputted into one visible neuron of the visible layer 602. An output of the visible layer 602 may serve as an input to the hidden layer 604. In some embodiments, each of the visible neurons in the visible layer 602 may be connected to each of the hidden neurons in the hidden layer 604 as shown in FIG. 6. In some embodiments, each of the neurons of the trained RBM 600 may have a binary state (i.e., 0 or 1). Alternatively, a plurality of Guassian-Bernoulli neurons may be used in the trained RBM, and data may be inputted into the trained RBM without being normalized into a range from 0 to 1.

In some embodiments, the trained RBM 600 may be an energy-based model, for example, an energy-based model having a linear energy function. Merely by way of example, the energy level of each neuron of the trained RBM 600 may be determined according to Equation (15) as below:

$$E(v,h) = -\Sigma_i a_i v_i - \Sigma_j b_j h_j - \Sigma_{i,j} v_i h_j w_{ij}, \qquad \text{Equation (15)}$$

where $a_i$ refers to a bias of the $i^{th}$ visible neuron in the state $v_i$, $b_j$ refers to a bias of the $j^{th}$ hidden neuron in the state $h_j$, and $w_{ij}$ refers to a weight of the connection between the $i^{th}$ visible neuron and the $j^{th}$ hidden neuron.

Figure 7:
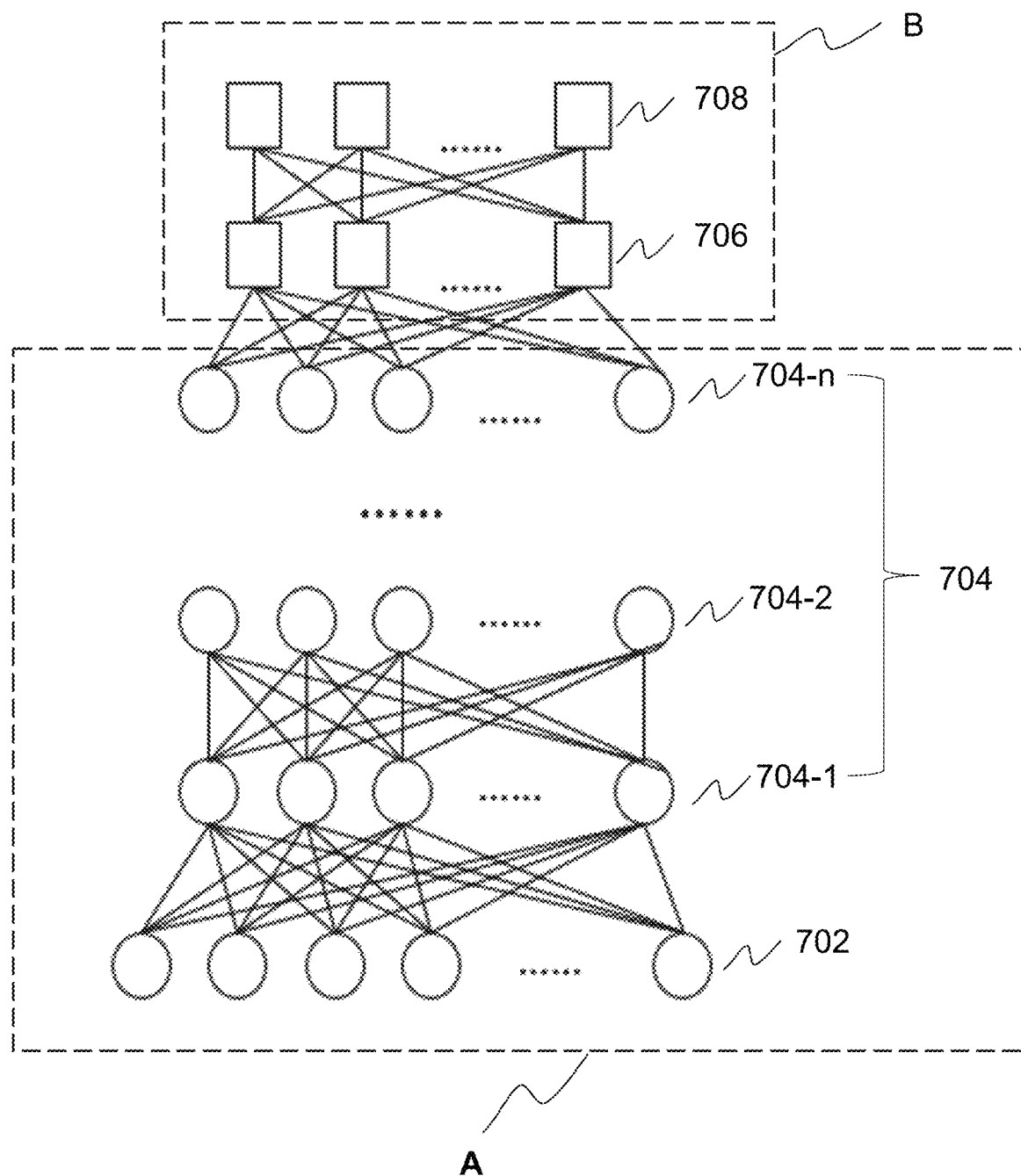
FIG. 7 is a schematic diagram illustrating an exemplary fault diagnosis model according to some embodiments of the present disclosure.

In some embodiments, the fault diagnosis model may have a same or similar configuration as an exemplary fault diagnosis model 700 as illustrated in FIG. 7. As shown in FIG. 7, the fault diagnosis model 700 may include a trained first component A and a trained second component B connected to the trained first component A. The trained first component A may include a plurality of stacked RMBs (also referred to as a Gaussian-Bernoulli RMB), which includes an input layer 702 and a plurality of hidden layers 704 (e.g., 704-1, 704-2, . . . , and 704-n). Each pair of adjacent layers among the input layer 702 and the hidden layers 704 may form one trained RBM. For example, the input layer 702 and the hidden layer 704-1 may form a first trained RBM, in which the input layer 702 may serve as a visible layer for receiving input data of the first trained RBM. As another example, the hidden layer 704-1 and the hidden layer 704-2 may form a second trained RBM, in which the hidden layer 704-1 may serve as a visible layer for receiving input data of the second trained RBM. The trained second component B may include a trained fully connected layer 706 and a trained output layer 708 connected to the trained fully connected layer 706. The fault diagnosis model 700 may be considered to a modification of a CNN model, which utilizes the trained RBMs to replace convolutional layers of the CNN model. The trained RBMs may be more suitable for processing one-dimensional features, such as the feature value(s) of the vibration signal. As such, the fault diagnosis model disclosed herein may result in a more accurate fault diagnosis result compared with the original CNN model.

The layers of the fault diagnosis model 700 may be connected in a feed-forward fashion, and an output of a certain layer may be provided as an input to a next layer immediately downstream and connected to the certain layer. Optionally, each neuron in the certain layer of the fault diagnosis model 700 may be connected to each neuron in the next layer. The input of each neuron in the certain layer may be a combination of the output of the neuron(s) in a previous layer of the certain layer. Merely by way of example, an input $\alpha_k$ of the $k^{th}$ neuron in the hidden layer 704-1 may be determined according to Equation (16) as below:

$$\alpha_k = \Sigma_{y=1}^d m_{yk} t_y,$$ Equation (16)

where $m_{yk}$ refers to a weight of the connection between the $k^{th}$ neuron in the hidden layer 704-1 and the $y^{th}$ neuron in the input layer 702, $t_y$ refers to the output of the $y^{th}$ neuron in the input layer 702, and d refers to the count (or number) of neurons in the input layer 702. As another example, an input $\beta_q$ of the $q^{th}$ neuron in the fully connected layer 706 may be determined according to Equation (17) as below:

$$\beta_q = \Sigma_{x=1}^g w_{xq} f_x,$$ Equation (17)

where $w_{xq}$ refers to a weight of a connection between the $q^{th}$ neuron in the fully connected layer 706 and the $x^{th}$ neuron in the hidden layer 704-n, $f_x$ refers to the output of the $x^{th}$ neuron in the hidden layer 704-n, and g refers to the count (or number) of neurons in the hidden layer 704-n. In some embodiments, an output of a middle layer of the fault diagnosis model 700 may include a feature map or a probability map.

It should be noted that the fault diagnosis model 700 illustrated in FIG. 7 may be illustrative and modified according to an actual need. For example, the fault diagnosis model 700 may include one or more additional components and/or one or more components described above (e.g., the fully connected layer 706) may be omitted. As another example, the fault diagnosis model 700 may include any number of layers, and the neurons in different layers may be connected in any suitable manner. In some embodiments, the number (or count) of layers of the fault diagnosis model 700 may be within a preset range, such as 10 to 50, 20 to 50, 30 to 50, 10 to 80, 20 to 80, or the like. Optionally, the number (or count) of layers of the fault diagnosis model 700 may be associated with the number (or count) of feature values of the vibration signal. For example, if the vibration signal of the target device has 27 feature values, the number (or count) of layers of the fault diagnosis model 700 may be in a range from 10 to 30, in order to improve the model accuracy and avoid data over fitting. In some embodiments, the fault diagnosis model 700 may have a rocket configuration as illustrated in FIG. 7. In some alternative embodiments, the fault diagnosis model 700 may have a pyramid configuration, a convex heptagon configuration, a convex pentagon configuration, etc.

It should be noted that the above description of the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the operations of the process 500 are intended to be illustrative. The process 500 may be accomplished with one or more additional operations not described and/or without one or more of the operations herein discussed. Additionally, the order in which the operations of the process 500 described above is not intended to be limiting.

For example, the process 500 may include an additional operation in which the processing device 140A transmits the fault diagnosis result to a terminal device for display. In some embodiments, the process 500 may include an additional operation in which the processing device 140A may record the fault condition of the target device and/or generate a notification regarding the fault condition. For example, the fault condition of the target device may be stored in a storage device for further inspection and/or used as training data in training and/or updating a fault diagnosis model. As another example, if it is determined that the target device has a fault, an alarm signal, such as a light signal, a sound signal, a vibration signal, or the like, may be transmitted to a user of the fault diagnosis system 100.

In addition, the above descriptions regarding the fault diagnosis model are merely provided for illustration purposes. The fault diagnosis model may include any suitable type of neural network components. Merely by way of example, the trained first component of the fault diagnosis model may include one or more models other than the trained RBMs, such as one or more other types of generative stochastic networks (GSN) (e.g., a radial basis function).

Figure 8:
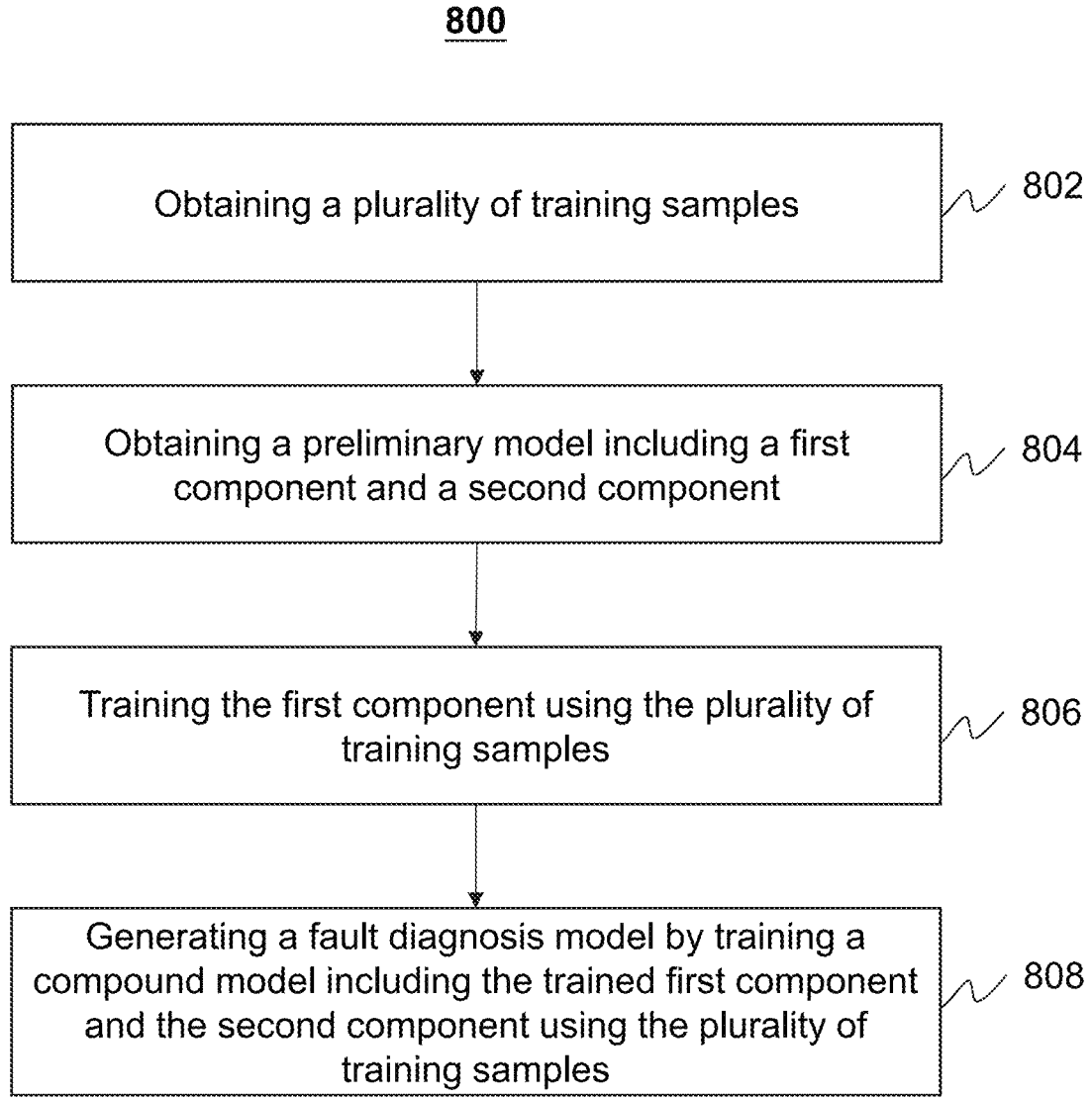
FIG. 8 is a flowchart illustrating an exemplary process for generating a fault diagnosis model according to some embodiments of the present disclosure.

FIG. 8 is a flowchart illustrating an exemplary process for generating a fault diagnosis model according to some embodiments of the present disclosure. In some embodiments, process 800 may be executed by the fault diagnosis system 100. For example, the process 800 may be implemented as a set of instructions (e.g., an application) stored in a storage device (e.g., the storage device 150, the storage 220, and/or the storage 390). In some embodiments, the processing device 140B (e.g., the processor 210 of the computing device 200, the CPU 340 of the mobile device 300, and/or one or more modules illustrated in FIG. 4B) may execute the set of instructions and may accordingly be directed to perform the process 800.

In 802, the processing device 140B (e.g., the acquisition module 440) may obtain a plurality of training samples.

Each of the plurality of training samples may include one or more sample feature values of a sample vibration signal of a sample device and a sample fault condition of the sample device. As used herein, a sample device may be a device that has a known fault condition (also be referred to as the sample fault condition). For example, the sample device may be a device that broke down and was diagnosed by, e.g., an engineer manually and/or a computing device automatically, thus having a known fault type. As another example, the sample device may be a device that operates normally and does not have a fault. The sample device may be of the same type of device as the target device as described in connection with FIG. 5.

A sample vibration signal of a sample device may refer to a vibration signal of the sample device. The sample vibration signal of a sample device may be similar to the vibration signal of the target device as described in connection with 502. A sample feature value of a sample vibration signal may refer to a feature value (e.g., a value of a statistical coefficient) of the sample vibration signal. For a training sample, the sample feature value(s) of a sample vibration signal of the corresponding sample device may be similar to the feature value(s) of the vibration signal of the target device as described in connection with 504. For example, for each training sample, the sample feature value(s) of the corresponding sample vibration signal may be determined in at least one of a frequency domain, a time domain, or a time-frequency domain. In some embodiments, for each training sample, the sample feature value(s) of the corresponding sample vibration signal may include at least one of a Kurtosis factor, a Skewness factor, a Crest Factor, a clearance factor, a shape factor, an impulse indicator, a variance, a denominator of clearance factor, an absolute mean value, or the like, or any combination thereof.

In some embodiments, a training sample may be previously generated and stored in a storage device (e.g., the storage device 150, the storage 220, the storage 390, or an external source). For example, for a device that has been broken down and diagnosed by an engineer, its corresponding historical vibration signal and historical diagnosis record may be stored in the storage device 150, and its corresponding sample feature value(s) may be determined by a computing device (e.g., the processing device 140) and stored in the storage device 150. The processing device 140B may retrieve the historical vibration signal, the historical diagnosis record, and the sample feature value(s) of the device from the storage device 150 as a training sample. Alternatively, the historical vibration signal and the historical diagnosis record may be stored and obtained from the storage device 150, and the sample feature value(s) may be determined by the processing device 140B by analyzing the historical vibration signal according to, for example, Equations (6) to (14) as described in connection with FIG. 5.

In 804, the processing device 140B (e.g., the acquisition module 440) may obtain a preliminary model.

The preliminary model may be any type of neural network model that is to be trained as the fault diagnosis model. In some embodiments, the preliminary model may include at least one RBM. In some embodiments, the preliminary model may include a first component and a second component connected to the first component. The first component may include a plurality of stacked RBMs. The second component may include a fully connected layer and an output layer. More descriptions regarding the RBM, the fully connected layer, and the output layer may be found elsewhere in the present disclosure. See, e.g., FIGS. 6 and 7 and relevant descriptions thereof.

In some embodiments, the preliminary model to be trained may include one or more model parameters. Exemplary model parameters may include the number (or count) of layers, the number (or count) of neurons in each layer, a loss function, or the like, or any combination thereof. Before training, the preliminary model may have one or more initial parameter values of the model parameter(s). In the training of the preliminary model, the values of the model parameter(s) of the preliminary model may be updated. In some embodiments, the number (or count) of layers of the preliminary model may be within a preset range, such as 10 to 50, 20 to 50, 30 to 50, 10 to 80, 20 to 80, or the like. In some embodiments, the number (or count) of layers of the preliminary model may be associated with the number (or count) of sample feature values of each training sample. For example, if each training sample has 27 sample feature values, the number (or count) of layers of the preliminary model may be in a range from 10 to 30, in order to improve the model accuracy and avoid data over fitting.

In some embodiments, the preliminary model may be trained using the training samples according to a model training process, during which the first component and the second component may be jointly trained. In some alternative embodiments, the first component and the second component may be trained in sequence during the model training process. The first component and the second component may be suitable for different training strategies, for example, an energy-based training strategy and a loss function-based training strategy, respectively. By training the first component and the second component separately using different training strategies may improve the accuracy and the reliability of the resulting fault diagnosis model. For illustration purposes, the following descriptions are described with reference to an exemplary model training process, during which the first component and the second component are trained in sequence, and not intended to limit the scope of the present disclosure.

In 806, the processing device 140B (e.g., the training module 450) may train the first component using the plurality of training samples.

As aforementioned, the first component may include a plurality of stacked RBMs. The stacked RBMs may include a plurality of layers (e.g., an input layer and a plurality of hidden layers) and a plurality of neurons (e.g., a plurality of visible neurons and a plurality of hidden neurons). In some embodiments, the first component may be trained according to any suitable machine training algorithm, such as a greedy layer-wise unsupervised learning algorithm, a supervised learning algorithm, a Gibbs sampling contrastive divergence algorithm, or the like. In some embodiments, the first component may be trained using an energy-based training strategy. The training of the first component may include an iterative operation including one or more iterations to iteratively update parameter value(s) of model parameter(s) of the first component. For example, during a current iteration of the iterative operation, the processing device 140B may determine an energy level of each of the plurality of neurons in an updated first component determined in a previous iteration based on the sample feature value(s) of each training sample. In some embodiments, the sample feature value(s) of each training sample may be inputted into the visible neurons of the updated first component, and an energy level of each neuron in the updated first component may be determined according to Equation (15) as described in connection with FIG. 6.

The processing device 140B may further determine whether a first termination condition is satisfied in the current iteration based on the determined energy levels. In some embodiments, the first termination condition may be associated with the lowest energy level among the energy levels of the neurons in the updated first component. For example, the processing device 140B may determine the lowest energy level, and determine whether the lowest energy level exceeds a threshold energy level or a difference of the lowest energy levels determined in the current iteration and the previous iteration is within a threshold value, etc. In response to a determination that the lowest energy level exceeds the threshold energy level or the difference of the lowest energy levels is within the threshold value, the processing device 140B may determine that the first termination condition is satisfied. In some alternative embodiments, the first termination condition may be that a certain count of iterations has been performed in training the first component.

In response to a determination that the first termination condition is satisfied in the current iteration, the processing device 140B may designate the updated first component as a trained first component. In response to a determination that the first termination condition is not satisfied in the current iteration, the processing device 140B may further update the updated first component, wherein the newly updated first component may be further trained in a next iteration. For example, the count of neurons in a hidden layer of the updated first component and/or a weight of a connection between different neurons may be modified to further update the updated first component.

In 808, the processing device 140B (e.g., the training module 450) may generate the fault diagnosis model by training a compound model including the trained first component and the second component using the plurality of training samples.

After the first component is trained, the trained first component in combination with the second component may form the compound model. For example, the second component may include the fully connected layer and the output layer as described in connection with 804. The fully connected layer may be connected to the last layer of the trained first component in the compound model to receive an output from the trained first component during the training of the compound model.

In some embodiments, the training of the compound model may include a second iterative operation including one or more second iterations to iteratively update parameter value(s) of model parameter(s) of the compound model. For example, during a current second iteration, the processing device 140B may determine a predicted fault condition of the sample device of each training using an updated compound model determined in a previous second iteration. Merely by way of example, the sample feature value(s) of each training sample may be inputted into the updated compound model, and the updated compound model may output the predicted fault condition of the corresponding sample device (e.g., whether the corresponding sample device has a fault or not, a predicted fault type of the corresponding sample device). The processing device 140B may further determine a value of a loss function based on the sample fault condition and the predicted fault condition of the sample device of each training sample. The loss function may be configured to measure a difference between the sample fault condition and the predicted fault condition of the sample device of each training sample, wherein the difference may indicate the accuracy of the updated compound model. Exemplary loss functions may include a 0-1 loss function, a logistic loss function, a cross-entropy loss function, an exponential loss function, etc.

Based on the value of the loss function, the processing device 140B may determine whether a second termination condition is satisfied in the current second iteration. An exemplary second termination condition may be that the value of the loss function obtained in the current second iteration is less than a threshold value. Other exemplary second termination conditions may include that a certain count of second iterations has been performed, that the loss function converges such that the difference of the values of the loss function obtained in a previous second iteration and the current second iteration is within a threshold value, etc. Upon a determination that the second termination condition is satisfied in the current second iteration, the processing device 140B may designate the updated compound model in the current iteration as the fault diagnosis model. Upon a determination that the second termination condition is not satisfied in the current second iteration, the processing device 140B may further update the updated compound model by updating the second model in the updated compound model. For example, the processing device 140B may update the value(s) of the model parameter(s) of the fully connected layer and/or the outputted layer in the updated compound model based on the value of the loss function according to, for example, a backpropagation algorithm. The newly updated compound model may be further trained in a next second iteration.

It should be noted that the above description of the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the operations of the process 800 are intended to be illustrative. The process 800 may be accomplished with one or more additional operations not described and/or without one or more of the operations herein discussed. Additionally, the order in which the operations of the process 800 described above is not intended to be limiting. In some embodiments, after the fault diagnosis model is generated, the processing device 140B may further test the fault diagnosis model using a set of testing samples. Additionally, or alternatively, the processing device 140B may update the fault diagnosis model periodically or irregularly based on one or more newly-generated training samples (e.g., new vibration signal generated in fault diagnosis).

It will be apparent to those skilled in the art that various changes and modifications can be made in the present disclosure without departing from the spirit and scope of the disclosure. In this manner, the present disclosure may be intended to include such modifications and variations if the modifications and variations of the present disclosure are within the scope of the appended claims and the equivalents thereof.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely as hardware, entirely as software (including firmware, resident software, micro-code, etc.) or as a combined software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter lies in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate a certain variation (e.g., ±1%, ±5%, ±10%, or ±20%) of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable. In some embodiments, a classification condition used in classification is provided for illustration purposes and modified according to different situations. For example, a classification condition that "a probability value is greater than the threshold value" may further include or exclude a condition that "the probability value is equal to the threshold value".

What is claimed is:

1. A system for fault diagnosis, comprising:
at least one storage device including a set of instructions; and
at least one processor configured to communicate with the at least one storage device, wherein when executing the set of instructions, the at least one processor is configured to direct the system to perform operations including:
acquiring a vibration signal of a target device;
determining at least one feature value of the vibration signal; and
determining a fault condition of the target device by applying a fault diagnosis model to the at least one feature value, wherein the fault diagnosis model is obtained by training a preliminary model at least including a first component, the first component including a plurality of stacked Restrictive Boltzmann Machines (RBMs), and the training of the first component including an iterative operation including one or more iterations, an iteration of the iterative operation including:
determining, based on each of a plurality of training samples, an energy level of each of a plurality of neurons in an updated first component determined in a previous iteration;
determining, among the energy levels of the plurality of neurons in the updated first component, a lowest energy level;
determining whether the lowest energy level exceeds a threshold energy level; and
in response to a determination that the lowest energy level does not exceed the threshold energy level, determining that a first termination condition is not satisfied, and further updating the updated first component to be used in a next iteration.

2. The system of claim 1, wherein the at least one feature value of the vibration signal is determined in at least one of a frequency domain, a time domain, or a time-frequency domain.

3. The system of claim 1, wherein the at least one feature value of the vibration signal includes at least one of a Kurtosis factor, a Skewness factor, a Crest Factor, a clearance factor, a shape factor, an impulse indicator, a variance, a denominator of clearance factor, or an absolute mean value.

4. The system of claim 1, wherein the target device is a medical imaging device or a portion thereof.

5. The system of claim 1, wherein the target device includes at least one of a cooling pump or a fan of a Magnetic Resonance Imaging (MRI) device.

6. The system of claim 1, wherein the plurality of stacked RBMs of the first component are energy-based models.

7. The system of claim 1, wherein the preliminary model further includes a second component connected to the first component, the second component including a fully connected layer and an output layer connected to the fully connected layer.

8. The system of claim 7, wherein the preliminary model is trained by a model training process including:
  training the first component using the plurality of training samples; and
  generating the fault diagnosis model by training a compound model including the trained first component and the second component using the plurality of training samples, the fault diagnosis model including the trained first component and the trained second component.

9. A system for generating a fault diagnosis model, comprising:
  at least one storage device storing a set of instructions; and
  at least one processor configured to communicate with the at least one storage device, wherein when executing the set of instructions, the at least one processor is configured to direct the system to perform operations including:
  obtaining a plurality of training samples, each of the plurality of training samples including at least one sample feature value of a sample vibration signal of a sample device and a sample fault condition of the sample device;
  obtaining a preliminary model including a first component and a second component, the first component including a plurality of stacked Restrictive Boltzmann Machines (RBMs), and the second component including a fully connected layer and an output layer;
  training the first component using the plurality of training samples, wherein the training of the first component includes an iterative operation including one or more iterations, an iteration of the iterative operation including:
  determining, based on each of the plurality of training samples, an energy level of each of a plurality of neurons in an updated first component determined in a previous iteration;
  determining, among the energy levels of the plurality of neurons in the updated first component, a lowest energy level;
  determining whether the lowest energy level exceeds a threshold energy level; and
  in response to a determination that the lowest energy level does not exceed the threshold energy level, determining that a first termination condition is not satisfied, and further updating the updated first component to be used in a next iteration; and
  generating the fault diagnosis model by training a compound model including the trained first component and the second component using the plurality of training samples, the fault diagnosis model including the trained first component and the trained second component.

10. The system of claim 9, wherein training the compound model including the trained first component and the second component includes the iterative operation including the one or more iterations, at least one iteration of the iterative operation including:
  for each of the plurality of training samples, determining a predicted fault condition of the sample device using an updated compound model determined in the previous iteration;
  determining, based on the sample fault condition and the predicted fault condition of the sample device of each training sample, a value of a loss function;
  determining, based on the value of the loss function, whether a second termination condition is satisfied; and
  in response to a determination that the second termination condition is not satisfied, further updating, based on the value of the loss function, the second component in the updated compound model while maintaining the trained first component.

11. The system of claim 9, wherein for each of the plurality of training samples, the at least one sample feature value of the sample vibration signal is determined in at least one of a frequency domain, a time domain, or a time-frequency domain.

12. The system of claim 9, wherein for each of the plurality of training samples, the at least one sample feature value of the sample vibration signal includes at least one of a Kurtosis factor, a Skewness factor, a Crest Factor, a clearance factor, a shape factor, an impulse indicator, a variance, a denominator of clearance factor, or an absolute mean value.

13. The system of claim 9, wherein the sample device of each of the plurality of training samples includes at least one a cooling pump or a fan of a Magnetic Resonance Imaging (MRI) device.

14. A method for fault diagnosis implemented on a computing device having at least one processor and at least one storage device, the method comprising:
  acquiring a vibration signal of a target device;
  determining at least one feature value of the vibration signal; and
  determining a fault condition of the target device by applying a fault diagnosis model to the at least one feature value, wherein the fault diagnosis model is obtained by training a preliminary model at least including a first component, the first component including a plurality of stacked Restrictive Boltzmann Machines (RBMs), and the training of the first component including an iterative operation including one or more iterations, an iteration of the iterative operation including:
  determining, based on each of a plurality of training samples, an energy level of each of a plurality of neurons in an updated first component determined in a previous iteration;
  determining, among the energy levels of the plurality of neurons in the updated first component, a lowest energy level;

determining whether the lowest energy level exceeds a threshold energy level; and in response to a determination that the lowest energy level does not exceed the threshold energy level, determining that a first termination condition is not satisfied, and further updating the updated first component to be used in a next iteration.

15. The method of claim 14, wherein the at least one feature value of the vibration signal is determined in at least one of a frequency domain, a time domain, or a time-frequency domain.

16. The method of claim 14, wherein the plurality of stacked RBMs of the first component are energy-based models.

17. The method of claim 14, wherein the preliminary model further includes a second component connected to the first component, the second component including a fully connected layer and an output layer connected to the fully connected layer.

18. The method of claim 17, wherein the preliminary model is trained by a model training process including:

training the first component using the plurality of training samples; and generating the fault diagnosis model by training a compound model including the trained first component and the second component using the plurality of training samples, the fault diagnosis model including the trained first component and the trained second component.

19. The method of claim 14, wherein the at least one feature value of the vibration signal includes at least one of a Kurtosis factor, a Skewness factor, a Crest Factor, a clearance factor, a shape factor, an impulse indicator, a variance, a denominator of clearance factor, or an absolute mean value.

20. The method of claim 14, wherein the target device is a medical imaging device or a portion thereof.

* * * * *